United States Patent
Samson et al.

(10) Patent No.: US 6,297,417 B1
(45) Date of Patent: *Oct. 2, 2001

(54) ALKYLATION/TRANSALKYLATION PROCESS WITH PRETREATMENT OF THE ALKYLATION/TRANSALKYLATION FEEDSTOCK

(75) Inventors: Mohammed S. U. Samson; Matheus J. M. Van der Aalst; Garmt R. Meima, all of Terneuzen (NL); Guo-shuh John Lee; Juan M. Graces, both of Midland, MI (US)

(73) Assignee: The Dow Chemical Company, Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 29 days.

(21) Appl. No.: 09/252,384

(22) Filed: Feb. 18, 1999

Related U.S. Application Data

(63) Continuation of application No. PCT/US97/14650, filed on Aug. 20, 1997, which is a continuation of application No. 08/700,255, filed on Aug. 20, 1996, now abandoned.

(51) Int. Cl.[7] .............................. C07C 2/66; C07C 15/08
(52) U.S. Cl. ..................... 585/448; 585/467; 585/485; 585/470
(58) Field of Search ................................. 585/448, 467, 585/475, 470, 446

(56) References Cited

U.S. PATENT DOCUMENTS

| | | | |
|---|---|---|---|
| 2,498,567 | 2/1950 | Morris et al. | 260/671 |
| 2,667,519 | 1/1954 | Paltz et al. | 260/671 |
| 2,943,118 | 6/1960 | Cahn et al. | 260/671 |
| 3,931,350 | 1/1976 | Sparks | 260/671 B |
| 4,008,261 | 2/1977 | Brown et al. | 260/448.2 E |
| 4,319,067 | 3/1982 | Kreeger | 585/459 |
| 4,358,362 | 11/1982 | Smith et al. | 208/91 |
| 4,665,255 | 5/1987 | Chang et al. | 585/467 |
| 4,783,566 | 11/1988 | Kocal et al. | 585/415 |
| 4,795,545 | 1/1989 | Schmidt | 208/91 |
| 4,891,448 | 1/1990 | Garces et al. | 568/628 |
| 4,891,458 | 1/1990 | Innes et al. | 585/323 |
| 4,921,946 | 5/1990 | Kocal et al. | 585/444 |
| 5,030,786 | 7/1991 | Shamshoum et al. | 585/467 |
| 5,081,323 | 1/1992 | Innes et al. | 585/449 |
| 5,134,242 | * 7/1992 | Le et al. | 585/533 |
| 5,177,285 | 1/1993 | Van Opdorp et al. | 585/467 |
| 5,198,595 | 3/1993 | Lee et al. | 585/467 |
| 5,243,116 | 9/1993 | Lee et al. | 585/467 |
| 5,245,094 | 9/1993 | Kocal | 585/323 |
| 5,300,722 | 4/1994 | Steigelmann et al. | 585/467 |

FOREIGN PATENT DOCUMENTS

| | | |
|---|---|---|
| 0 366 515 | 5/1990 | (EP) . |
| 0 780 354 A1 | 6/1997 | (EP) . |
| 59-137426 | 8/1984 | (JP) . |
| 4-198139 | 7/1992 | (JP) . |
| 789464 | 6/1978 | (SU) . |
| 89/12613 | 12/1989 | (WO) . |
| 93/00992 | 1/1993 | (WO) . |

* cited by examiner

Primary Examiner—Marian C. Knode
Assistant Examiner—Thuan D. Dang
(74) Attorney, Agent, or Firm—Marie F. Zuckerman

(57) ABSTRACT

A process of preparing an alkylated benzene or mixture of alkylated benzenes involving contacting a benzene feedstock with a solid acid, such as an acidic clay or acid zeolite, in a pretreatment zone at a temperature greater than about 130° C. but less than about 300° C. to form a pretreated benzene feedstock, and thereafter contacting the pretreated benzene feedstock with (a) an alkylating agent in an alkylation zone or (b) a transalkylating agent in a transalkylation zone, in the presence of an alkylation/transalkylation catalyst so as to prepare the alkylated benzene or mixture of alkylated benzenes. The pretreatment step improves the lifetime of the alkylation/transalkylation catalyst. Preferred products are ethylbenzene and cumene.

23 Claims, 2 Drawing Sheets

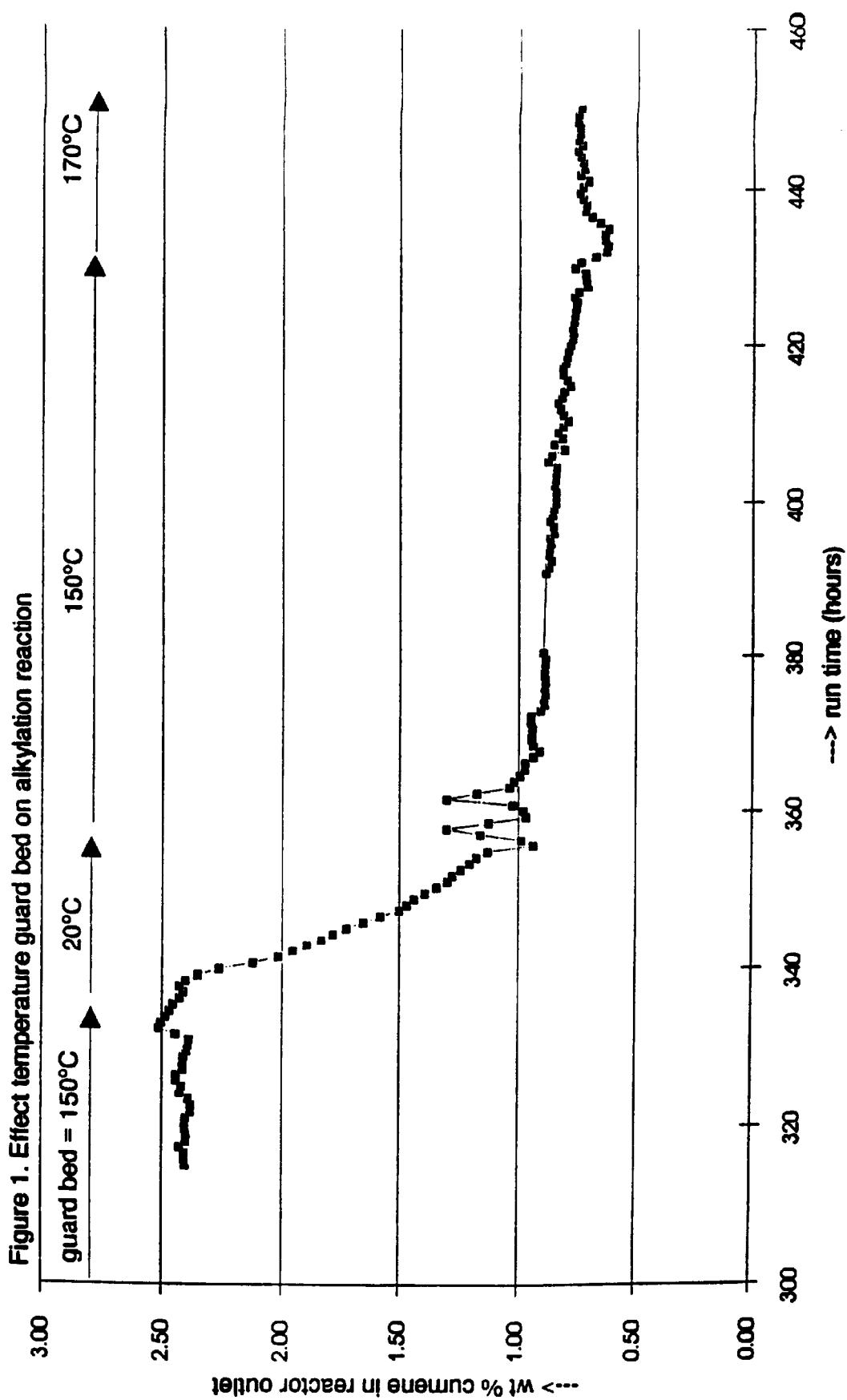

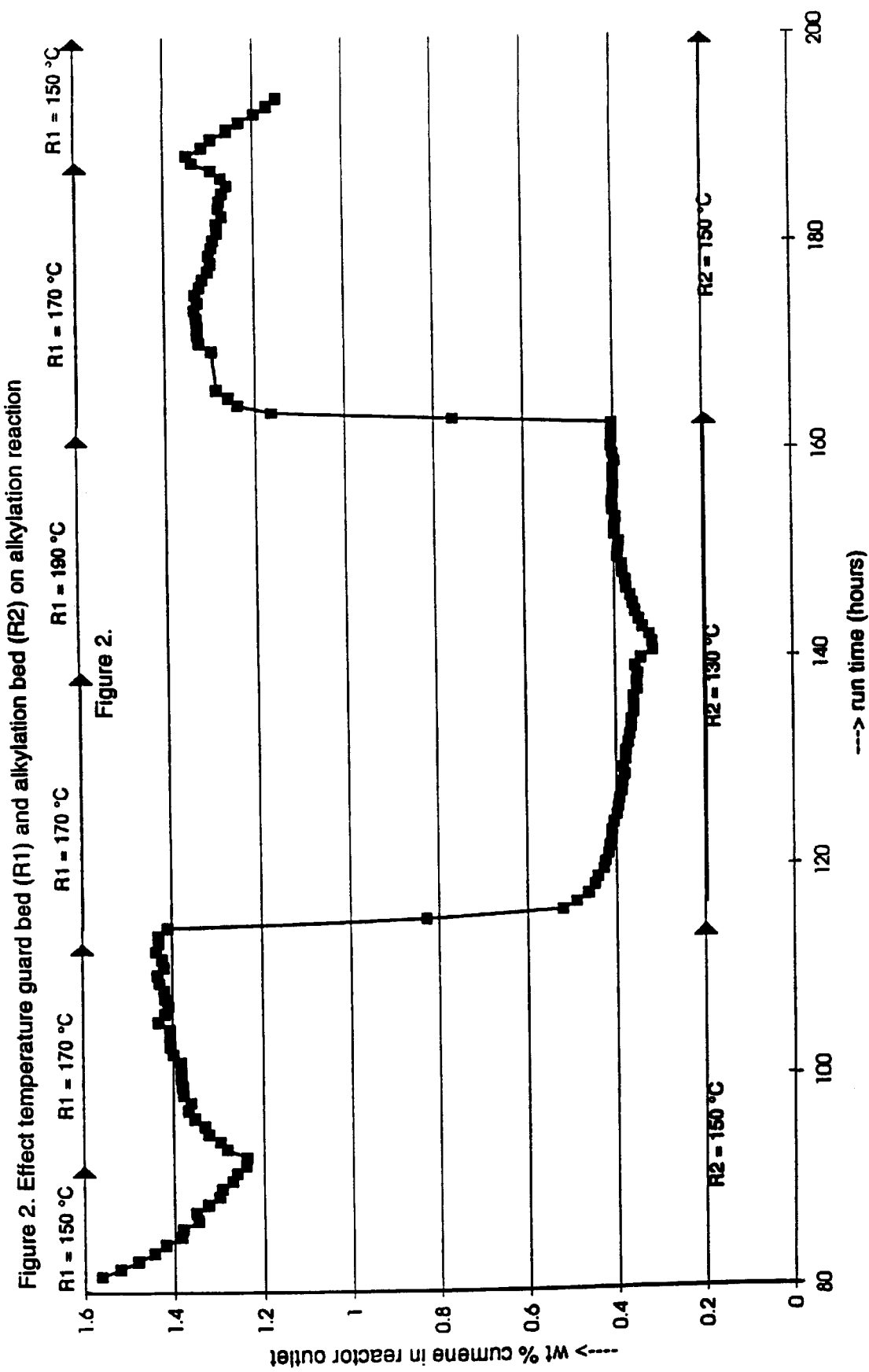

US 6,297,417 B1

ALKYLATION/TRANSALKYLATION PROCESS WITH PRETREATMENT OF THE ALKYLATION/TRANSALKYLATION FEEDSTOCK

CROSS-REFERENCE TO RELATED APPLICATIONS

This application is a continuation of International Patent Application No. PCT/US97/14650, filed Aug. 20, 1997, which was a continuation of U.S. patent application Ser. No. 08/700,255, filed Aug. 20, 1996, now abandoned.

BACKGROUND OF THE INVENTION

In one aspect, this invention pertains to a process for the production of alkylated benzenes by alkylating benzene with an alkylating agent or by transalkylating benzene with a transalkylating agent in the presence of a catalytic zeolite. In another aspect, this invention pertains to a method of increasing the lifetime of a zeolite alkylation/transalkylation catalyst.

Alkylation and transalkylation processes employing zeolite catalysts are useful for producing monoalkylated and dialkylated benzenes. Monoalkylated benzenes, such as ethylbenzene and cumene, are highly valuable bulk chemicals. Ethylbenzene, for example, is used in the preparation of styrene, a precursor to polystyrene. Cumene is used in the preparation of phenol and acetone. Dialkylated benzenes, such as para-di(isopropyl)benzene, are useful starting materials for preparing the corresponding dicarboxylic acid or dihydroxy benzenes, for example, hydroquinone.

It is known to alkylate benzene with an olefin in the presence of a catalytic zeolite. With regard to the use of dealuminated acid mordenite zeolite, reference is made to U.S. Pat. Nos. 4,891,448, 5,198,595, 5,243,116, and European Patent publication 0,366,515. With regard to the use of zeolite ZSM-5, reference is made, for example, to U.S. Pat. No. 4,665,255. With regard to the use of zeolite beta, reference is made to U.S. Pat. Nos. 4,891,458, and 5,081,323.

It is known that the lifetime of a zeolite alkylation catalyst is shortened by polymerization of the olefinic alkylating agent and by formation of carbonaceous deposits (polyaromatics). Periodically, an alkylation reactor, whether operating in a liquid or gas phase, must be shut down to regenerate the catalyst. Regeneration is typically effected by controlled burning off of the condensed polymers and carbonaceous deposits in air at elevated temperature, for example, at a temperature between about 400° C. and about 700° C. Disadvantageously, repeated regeneration at elevated temperatures can damage the zeolite.

It is known, for example, from PCT application WO 89/12613, that the lifetime of an alkylation catalyst can be improved by adding hydrogen to the alkylation feedstream. Disadvantageously, this process requires a hydrogen supply which increases expenses and necessitates a complex engineering design.

Some patents, such as PCT application WO 93/00992, disclose the addition of water to an alkylation feed or alkylation/transalkylation molecular sieve catalyst to increase the lifetime of the catalyst. In contrast, other patents, such as U.S. Pat. No. 5,030,786, teach an increase in catalyst lifetime on decreasing the concentration of water in the alkylation feedstream.

It is also known, such as from U.S. Pat. Nos. 4,358,362 and 5,245,094, to enhance the activity of a zeolite catalyst employed in a catalytic conversion process by pretreating the process feedstock over a molecular sieve zeolite. This method has been illustrated for pretreating hydrocarbon feedstocks used in dewaxing processes and for pretreating $C_{6\text{-}20}$ olefinic feedstocks derived from the dehydrogenation of long-chain paraffins, for use in alkylation processes.

It would be advantageous to find an effective method for improving the lifetime of a zeolite catalyst employed in an alkylation or transalkylation process, preferably for preparing ethylbenzene or cumene. It would be more advantageous if the regeneration method could be used without damage to the catalyst and without undue expense and complex engineering.

SUMMARY OF THE INVENTION

In one aspect, this invention is a process of alkylating a benzene feedstock with an alkylating agent or of transalkylating a benzene feedstock with a transalkylating agent to form an alkylated benzene product. The term "benzene feedstock" embraces in its scope unsubstituted benzene as well as substituted benzenes, as described hereinafter. The process comprises contacting the benzene feedstock with a solid acid in a pretreatment zone at a temperature greater than about 130° C. but less than about 300° C. to form a pretreated benzene feedstock, and thereafter contacting the pretreated benzene feedstock with (a) an alkylating agent in an alkylation zone or (b) a transalkylating agent in a transalkylation zone, the contacting occurring in the presence of an alkylation/transalkylation catalyst under reaction conditions sufficient to produce an alkylated benzene or mixture of alkylated benzenes.

In another aspect, this invention is a method of increasing the lifetime of a zeolite catalyst employed in an alkylation or transalkylation process. The method involves pretreating an alkylation or transalkylation feedstream prior to contacting it with the alkylation/transalkylation catalyst. The pretreatment procedure, as noted hereinabove, comprises contacting the aforementioned benzene feedstock of an alkylation or transalkylation feedstream with a solid acid at a temperature greater than about 130° C. but less than about 300° C.

The aforementioned process of this invention, which involves pretreating a benzene feedstock, provides an effective method of extending the lifetime of an alkylation/transalkylation catalyst. As further advantages, the pretreatment method is inexpensive, easy to implement, and not damaging to the catalyst. Alkylation and transalkylation processes improved by the pretreatment method of this invention are beneficially employed in the preparation of valuable monoalkylated and dialkylated benzenes, including the alkylation of benzene with ethylene or propylene to form ethylbenzene or cumene and the corresponding diethyl or di(isopropyl)benzenes, or alternatively, the transalkylation of benzene with polyethylbenzene or poly(isopropyl) benzene to form ethylbenzene or cumene.

DESCRIPTION OF THE DRAWINGS

FIG. 1 of the drawings is a plot of the weight percent cumene in the alkylation reactor outlet as a function of time and pretreatment bed (guard bed) temperature.

FIG. 2 of the drawings is a plot of the weight percent cumene in the alkylation reactor outlet as a function of time, pretreatment bed (guard bed) temperature (R1), and alkylation reactor temperature (R2).

DETAILED DESCRIPTION OF THE INVENTION

The process of this invention produces an alkylated benzene or mixture of alkylated benzenes, preferably, monoalkylated and/or dialkylated benzenes. More preferably, the process of this invention produces a $C_{2-5}$ alkylated benzene or mixture of $C_{2-5}$ alkylated benzenes. Most preferably, the monoalkylated benzene is ethylbenzene or cumene. Most preferably, the dialkylated benzene is diethylbenzene or di(isopropyl)benzene. The process involves pretreating a benzene feedstock by contacting the same with a solid acid in a pretreatment zone at a temperature greater than about 130° C. but less than about 300° C., and thereafter contacting the pretreated benzene with an alkylating agent in an alkylation zone or with a transalkylating agent in a transalkylation zone in the presence of a zeolite alkylation/transalkylation catalyst.

In a preferred embodiment, this invention is a method of preparing ethylbenzene or cumene comprising contacting unsubstituted benzene with a solid acid in a pretreatment zone at a temperature greater than about 130° C. but less than about 300° C., and thereafter contacting the pretreated benzene with ethylene or propylene in an alkylation zone in the presence of a zeolite alkylation catalyst under reaction conditions sufficient to produce ethylbenzene or cumene. In a more preferred embodiment, the alkylation process is conducted in a liquid phase with a catalyst selected from the group consisting of acidic zeolites mordenite, beta, omega, and MCM-22. In another more preferred embodiment, the alkylation is conducted in a vapor phase with a catalyst selected from the group consisting of acidic zeolites mordenite and ZSM-5, and porous crystalline magnesium silicates.

In yet another preferred embodiment, this invention is a process of preparing ethylbenzene or cumene comprising contacting unsubstituted benzene with a solid acid in a pretreatment zone at a temperature greater than about 130° C. but less than about 300° C., and thereafter contacting the pretreated benzene with a polyethylated benzene or poly (isopropylated) benzene in a transalkylation zone in the presence of a zeolite transalkylation catalyst under reaction conditions sufficient to produce ethylbenzene or cumene. In a more preferred embodiment, the transalkylation process is conducted in a liquid phase with a catalyst selected from the group consisting of acidic zeolites mordenite, beta, and ZSM-12.

The alkylation feedstream contains a benzene component and an alkylating agent. The benzene component can be unsubstituted benzene or a substituted benzene. References broadly made herein to the "benzene component" or "benzene feedstock" are meant to include both unsubstituted and substituted species of benzene. Substituted benzenes include benzenes substituted with alkyl, preferably $C_{1-10}$ alkyl, and/or hydroxyl groups. Toluene, xylene, ethylbenzene, cumene, and phenol are examples of suitable substituted benzenes. Preferably, the benzene component of the feedstream contains benzene in its unsubstituted form. More preferably, the benzene component is essentially free of fluoride-containing impurities. The term "essentially free" means that the fluoride concentration is less than about 100 parts per billion (ppb) by weight.

The alkylating agent can be any compound which is capable of alkylating the benzene component to an alkylated benzene. Preferably, the alkylating agent is an olefin, more preferably, an aliphatic or cycloaliphatic olefin having from 2 to about 12 carbon atoms. Even more preferably, the alkylating agent is an aliphatic olefin having from 2 to about 5 carbon atoms. Most preferably, the olefinic alkylating agent is ethylene or propylene, and the preferred monoalkylated products are ethylbenzene and cumene, respectively. Likewise, the preferred dialkylated products are diethylbenzene and di(isopropyl)benzene, respectively.

The transalkylation feedstream contains a benzene component identical to that described hereinabove and a transalkylating agent. Preferably, the benzene component is unsubstituted benzene. Typically, the transalkylating agent comprises a polyalkylated benzene. The polyalkylated benzene contains a plurality of alkyl moieties, each independently containing from 2 to about 12 carbon atoms, more preferably, 2 to about 5 carbon atoms. Even more preferably, the polyalkylated benzene is a dialkylated or trialkylated benzene. Most preferably, the polyalkylated benzene is diethylbenzene or di(isopropyl)benzene, and the monoalkylated product is ethylbenzene or cumene, respectively. The polyalkylated benzene may also be ring substituted with one or more hydroxyl moieties or other moieties unreactive in the alkylation or transalkylation process.

The alkylation or transalkylation feedstream may also contain water. Preferably, the water is dissolved in the feedstream, rather than being present as free water in a separate phase. Preferably, the water concentration is less than about 200 parts per million (ppm) by weight, and more preferably, less than about 100 ppm by weight. If the water concentration exceeds the preferred range, then it is preferable to dry at least one of the alkylation or transalkylation feedstream components so as to reduce the water concentration of the alkylation or transalkylation feedstream to less than about 200 ppm. Preferably, the water is removed by conventional azeotropic distillation. An alternative drying procedure comprises sparging or purging any of the alkylation or transalkylation feedstream components with an inert gas, such as helium or nitrogen or argon, at a temperature ranging from about 10° C. to about 90° C., and preferably from about ambient, taken as 22° C., to about 60° C., until a water concentration of less than about 200 ppm is achieved. As a further alternative, one or more of the components of the alkylation or transalkylation feedstream can be contacted with a solid drying agent.

Any solid drying agent known to those skilled in the art may be used to reduce the water concentration in the alkylation or transalkylation feedstream. Non-limiting examples of suitable drying agents include aluminas, silicas, silica-aluminas, and zeolites. The aluminas, silicas, and silica-aluminas may be crystalline or amorphous. Zeolites are crystalline microporous aluminosilicates which have framework structures formally constructed from $(SiO_4)$ and $(AlO_4)$ tetrahedra that share vertices. Each framework topology contains a regular array of pores, channels, and/or cages that vary in size, shape, and dimensionality. Examples of suitable zeolites include erionite, chabazite, rho, gismondine, Linde 13X, Linde type A (LTA) molecular sieves, such as 3A, 4A, and 5A. A description of these zeolites, their structures, properties, and methods of synthesis can be found in the following references: *Zeolite Molecular Sieves,* Donald W. Breck, John Wiley & Sons, 1974; *Atlas of Zeolite Structure Types,* 3rd ed., W. M. Meier and D. H. Olson, Butterworth-Heinemann, 1992; and *Handbook of Molecular Sieves,* R. Szostak, Chapman & Hall, New York, 1992; which are incorporated herein by reference. Many of the suitable aluminas, silicas, silica-aluminas, and zeolites are commercially available. The preferred drying agents comprise LTA zeolites, including 3A, 4A, and 5A, in addition to Linde zeolite 13X and Selexsorb CDO® brand alumina.

In the general practice of the drying procedure with a solid drying agent, one or more components of the alkylation or transalkylation feedstream are passed in the liquid phase through a bed containing the drying agent, under conditions sufficient to lower the water concentration to a value no greater than about 200 ppm by weight. Typically, the sorbent temperature ranges from about 10° C. to about 90° C., and preferably, from about ambient, taken as about 22° C., to about 60° C. The pressure may range from subatmospheric to superatmospheric, but usually ranges from a pressure sufficient to maintain the alkylation or transalkylation feedstream component(s) in the liquid phase to a pressure of about 50 bar (5,000 kPa). Preferably, the pressure ranges from about 1 bar (100 kPa) to about 3 bar (300 kPa). The weight hourly space velocity of the component(s) which is(are) contacted with the adsorbent bed ranges from about 0.1 gram feed per gram drying agent per hour ($hr^{-1}$) to about 100 $hr^{-1}$.

Benzene and substituted benzenes can also contain oxygen and organic oxygenates. The equilibrium concentration of molecular oxygen which is dissolved in unsubstituted benzene at about 23° C. is about 300 ppm by weight, as measured by an oxygen analyzer, such as an Orbisphere Oxygen Analyzer Model 26083. For the purposes of this invention, "organic oxygenates" are defined as organic compounds which comprise carbon, hydrogen, and oxygen. Non-limiting examples of organic oxygenates, which may be found in benzene and substituted benzenes, include organic hydroperoxides, ketones, aldehydes, and phenols. The organic oxygenates may be natural impurities in the aromatic hydrocarbon as it is obtained from coal tar, or from a gasoline refinery, or from a benzene extraction unit, or a hydrodealkylation unit typically present at naphtha steam cracker facilities. Alternatively, the organic oxygenates may be produced by the reaction of oxygen with hydrocarbons present in the feed. In addition to oxygen and oxygenates, aromatic hydrocarbons may also contain small amounts of other impurities, including nitrogen-containing organic compounds, typically for example, traces of extraction solvents, such as N-methylpyrrolidone.

It is believed that low levels of the aforementioned impurities, even as low as in the parts per million range, may be detrimental to the lifetime of an alkylation/transalkylation catalyst. Unexpectedly, it has now been found that pretreatment of the alkylation/transalkylation feedstream, particularly at a temperature greater than about 130° C. but less than about 300° C., significantly improves the alkylation/transalkylation catalyst lifetime. It is believed that the pretreatment procedure removes or reduces the concentration of the aforementioned impurities, thereby beneficially increasing the catalyst lifetime. Such a belief, however, is only a theory and should not necessarily be binding in any way upon the process of this invention.

Thus, in accordance with the process of this invention the alkylation or transalkylation feedstream is pretreated by contacting the benzene feedstock with a solid acid at a temperature greater than about 130° C. but less than about 300° C. The benzene feedstock refers to the unsubstituted or substituted benzene component described hereinabove, but does not refer to the transalkylating agents. Suitable solid acids include amorphous and crystalline acid aluminas, silicas, and silica-aluminas; acidic clays, acid zeolites, and acidic mesoporous aluminosilicates. Zeolites are typically microporous, which means that they possess pores having a diameter or critical dimension between about 4 Angstroms (Å) and about 20 Å. For the purposes of this invention, mesoporous aluminosilicates will be those which contain pores having a diameter or critical dimension greater than about 20 Å up to about 200 Å. Non-limiting examples of suitable zeolites and mesoporous aluminosilicates include ZSM-5, ZSM-11, ZSM-35, clinoptilolite, ferrierite, stilbite, EU-1, MCM-22, and NU-87, as well as, mordenite, omega, beta, faujasites, including X and Y, gmelinite, ZSM-12, cancrinite, L, MCM-41, MCM-49, MCM-56, and MCM-58. Many of the aforementioned materials are commercially available. Descriptions of zeolites and mesoporous aluminosilicates, including their structures, properties, and methods of synthesis, can be found in the current literature, for example, in *Zeolite Molecular Sieves,* Donald W. Breck, op. cit.; *Atlas of Zeolite Structure Types,* 3rd ed., W. M. Meier and D. H. Olson, op. cit.; and *Handbook of Molecular Sieves,* R. Szostak, Chapman & Hall, New York, 1992, op. cit.; incorporated herein by reference. Preferably, the zeolite used in the pretreatment zone is the same type of zeolite which is used as a catalyst in the alkylation or transalkylation zone. Preferably, the zeolite used in the pretreatment zone is selected from the group consisting of zeolites mordenite, beta, ZSM-5, Y, L, omega, MCM-22, MCM-49, and MCM-56.

The silica/alumina molar ratio of the zeolite or mesoporous aluminosilicate used in the pretreatment zone may vary within a wide range, preferably, from about 5 to about 10,000. More preferably, the silica/alumina molar ratio ranges from about 5 to about 300.

The pretreatment zone may comprise any conventional reactor design, including continuous and intermittent flow, batch and fixed-bed reactors. Preferably, the pretreatment zone is a continuous flow, fixed-bed reactor. The pretreatment zone may be constructed as a separate reactor which is connected in series to an alkylation/transalkylation reactor. Alternatively, the pretreatment zone may comprise only one section of a reactor containing both pretreatment and alkylation or transalkylation zones. Alternatively, a multi-bed reactor may be used wherein the first bed comprises the pretreatment zone, wherein the alkylating/transalkylating agent is introduced at the second bed and further beds along a multi-bed chain, and wherein further along the chain a transalkylation reactor may be placed.

The process conditions under which the benzene component is contacted with the solid acid varies depending upon the particular benzene chosen and its substitution, as well as the solid acid employed. Usually, the contacting occurs at a temperature greater than about 130° C., preferably, greater than about 150° C., and more preferably, greater than about 165° C. Usually, the contacting occurs at a temperature less than about 300° C., preferably, less than about 250° C., and more preferably, less than about 225° C. Below about 130° C. the effectiveness of the pretreatment method may be reduced. Above about 300° C. undesirable side reactions may occur, and the pretreated benzene feedstock may be too hot for liquid phase alkylation/transalkylation processes. If the benzene component of the alkylation or transalkylation feedstream is an alkyl-substituted benzene, then the preferred contacting temperature is at the lower end of the temperature range, for example, from greater than about 130° C. to less than about 150° C. With alkyl-substituted benzenes at higher temperatures, undesirable processes, such as isomerization, disproportionation, and unwanted transalkylations may occur.

Generally, the benzene feedstock can be in a liquid or gaseous phase, preferably, the liquid phase. The pressure may range broadly from subatmospheric to superatmospheric, but preferably, is in a range from about 1 bar (100 kPa) to about 45 bar (4,500 kPa). In a liquid phase process, the weight hourly space velocity of the benzene component typically ranges from about 0.1 $hr^{-1}$ to about 1000 $hr^{-1}$, and preferably, ranges from about 1 $hr^{-1}$ to about 100 $hr^{-1}$. In a vapor phase process, the gas hourly space velocity of the benzene component typically ranges from about 1 hr$^{-1}$ to about 1000 hr$^{-1}$, and preferably, ranges from about 10 hr$^{-1}$ to about 100 hr$^{-1}$.

When the alkylation or transalkylation feedstream is pretreated by the method described hereinabove, then surprisingly the lifetime of the alkylation/transalkylation catalyst is significantly increased. The extent to which the lifetime is increased will depend upon the specific reagents treated, the specific process conditions, and the level of contamination in the feed.

Any alkylation/transalkylation catalyst can have its lifetime lengthened by the aforementioned process of this invention. Suitable catalysts include acidic zeolites and mesoporous aluminosilicates, as well as porous crystalline magnesium silicates. Non-limiting examples of specific catalysts include mordenite, ZSM-5, ZSM-12, beta, Y, omega, EU-1, NU-87, L, MCM-22, SSZ-25, MCM-36, MCM-49, MCM-56, and MCM-58. Some of these materials are commercially available, and methods for the preparation of all of these materials are known. For example, U.S. Pat. Nos. 5,198,595 and 5,243,116, and European patent publication 0,366,515 describe the preparation of dealuminated acid mordenites. Acid ZSM-5 and its preparation are described in U.S. Pat. No. 3,702,886. ZSM-12 is described in U.S. Pat. No. 3,832,449. Beta is described in U.S. Pat. Nos. 4,891,458 and 5,081,323; zeolite Y in U.S. Pat. No. 3,130,007; MCM-22 in U.S. Pat. Nos. 4,992,606 and 4,954,325; SSZ-25 in U.S. Pat Nos. 4,826,667, 5,149,894 and 5,421,992; MCM-36 in U.S. Pat. No. 5,258,565; MCM-49 in U.S. Pat. No. 5,236,575 and WO 94/29245; MCM-56 in U.S. Pat. No. 5,453,554; MCM-58 in WO 95/11196; and porous crystalline magnesium silicates in U.S. Pat. No. 4,499,320. Omega, EU-1, NU-87, and L are referenced in W. M. Meier and D. H. Olson, *Atlas of Zeolite Structure Types*, op. cit. The aforementioned references are incorporated herein by reference. Preferred alkylation/transalkylation catalysts include mordenite, beta, omega, MCM-22, EU-1, ZSM-5, and porous crystalline magnesium silicates.

A preferred form of the mordenite zeolite used in both the pretreatment zone and the alkylation/transalkylation zone is described in U.S. Pat. No. 4,891,448 and related U.S. Pat. Nos. 5,175,135; 5,198,595, and 5,243,116, which are incorporated herein by reference. This preferred catalyst is a dealuminated acid mordenite zeolite having a silica/alumina molar ratio of at least about 30:1 and a Symmetry Index, as determined by X-ray diffraction, of at least about 1.0. The catalyst preferably has a porosity such that the total pore volume is in the range from about 0.18 cc/g to about 0.45 cc/g, while the ratio of the combined mesopore and micropore volumes to the total pore volume is in the range from about 0.25 to about 0.75. As related to this mordenite, a micropore has a radius in the range of about 3 Angstrom (Å) units to 10 Å; a mesopore has a radius in the range of greater than 10 Å up to 100 Å; and a macropore has a radius in the range of greater than 100 Å up to 1000 Å. The preferred mordenite catalyst is prepared by a method comprising: (1) calcining in air or heating in an inert atmosphere an acidic mordenite having a silica/alumina molar ratio less than 30:1 and having a Symmetry Index between about 0.5 and about 1.3, more preferably between about 0.7 and about 1.3, and thereafter (2) treating the calcined or heated mordenite with strong acid under reaction conditions sufficient to yield a silica/alumina molar ratio of at least 30:1, and optionally (3) repeating the steps of (1) calcining or heating and (2) treating with strong acid at least once so as to remove additional alumina.

The alkylation or transalkylation process itself is conducted as generally described in the above-cited patents, for example, U.S. Pat. Nos. 4,891,448; 5,081,323; 5,198,595; and 5,243,116, incorporated herein by reference. In contrast to the prior art, hydrogen gas is preferably not added to the alkylation or transalkylation process of this invention. The contacting of the pretreated feedstream with the alkylating or transalkylating agent over the alkylation/transalkylation catalyst may occur in a reactor of any configuration. Batch-type and continuous reactors, such as fixed bed, slurry bed, fluidized bed, catalytic distillation, and countercurrent reactors, are suitable configurations for the contact. Preferably, the reactor is a fixed-bed, continuous flow reactor. The alkylation feedstream may be in the liquid or gaseous phase.

For the alkylation process, the ratio of the benzene component to catalyst may be any weight ratio which produces the desired alkylated benzene with relatively high selectivity. Preferred ratios will depend upon the way the process is operated. For example, in a continuous mode of operation and in the liquid phase, the weight hourly space velocity (WHSV) of the overall feed with respect to catalyst is preferably in the range from about 0.5 hr$^{-1}$ to about 100 hr$^{-1}$, more preferably, from about 0.5 hr$^{-1}$ to about 20 hr$^{-1}$. For the gas phase, the gas hourly space velocity (GHSV) preferably ranges between about 10 hr$^{-1}$ and 200 hr$^{-1}$.

The molar ratio of the benzene component to alkylating agent may vary depending on the identity of the alkylating agent, type of reaction such as batch or continuous, and reaction conditions such as temperature, pressure, and space velocity. In a continuous alkylation process, the molar ratio of the benzene component to alkylating agent is preferably at least about 1:1, more preferably, between about 1:1 and about 25:1.

The alkylation process conditions may be any which produce an alkylated benzene or mixture of alkylated benzenes. Typically, the temperature ranges between about 100° C. to about 550° C. When the benzene component and the alkylating agent are in the liquid phase, the process temperature preferably ranges between about 100° C. and about 300° C. When the benzene component and the alkylating agent are both in the vapor phase, the process temperature preferably ranges between about 350° C. and about 500° C. Typical alkylation pressures range from about 10 bar (1,000 kPa) to about 200 bar (20,000 kPa), preferably, from about 20 bar (2,000 kpa)to about 100 bar (10,000 kPa).

In a preferred embodiment, benzene and ethylene or propylene are contacted in the liquid phase with the preferred acid mordenite, beta, MCM-22, or omega. These catalysts exhibit high selectivity to ethylbenzene and cumene and exhibit catalyst lifetimes on the order of at least about 500 hours, and more preferably, at least about 1000 hours.

In another preferred embodiment, benzene and ethylene or propylene are contacted in the vapor phase with the preferred acid mordenite or with an acidic zeolite ZSM-5 or with a porous crystalline magnesium silicate. These catalysts also exhibit high selectivity to ethylbenzene and cumene and catalyst lifetimes on the order of at least about 500 hours, and more preferably, at least about 1000 hours. Moreover, the mordenite catalyst produces essentially no xylenes which, if formed, would be undesirable co-products.

For the transalkylation process in a continuous mode of operation, the WHSV of the transalkylation feed with respect to the transalkylation catalyst is preferably in the range from about 0.1 hr$^{-1}$ to about 100 hr$^{-1}$, more preferably, in the range from about 0.1 hr$^{-1}$ to about 20 hr$^{-1}$. In the transalkylation process, the ratio of the total moles of benzene groups present in the benzene and polyalkylated benzene to the total moles of alkylated groups on the polyalkylated benzene is preferably between about 1:1 and about 20:1. More preferably, this molar ratio is from about 2:1 to about 10:1. Typically, the transalkylation temperature is in the range from about 140° C. to about 300° C. Typical transalkylation pressures range from about 10 bar (1,000 kPa) to about 200 bar (20,000 kPa), and preferably, from about 20 bar (2,000 kPa) to about 100 bar (10,000 kPa).

Alkylated products are typically removed from the alkylation and transalkylation product streams by distillation. Unreacted benzene and/or alkylating agent may be recycled to the alkylation zone. Likewise, unreacted benzene and/or transalkylating agent may be recycled to the transalkylation zone. Typically, the recycle streams are not recycled into the pretreatment zone.

EXAMPLES

The following examples are presented to illustrate the claimed process of this invention. The examples illustrate the importance of the pretreatment zone temperature on alkylation/transalkylation catalyst stability. These examples, however should not be construed to limit the scope of this invention.

Example 1

Alkylation of Benzene with Propylene to Form Cumene

Benzene is alkylated with propylene to form cumene as follows. A pretreatment zone is connected in series to an alkylation zone. The pretreatment zone comprises a fixed-bed, continuous flow, tubular reactor (1.89 cm i.d.×100 cm length) containing an acidic mordenite zeolite (10 g). The alkylation zone comprises a fixed-bed, continuous flow, tubular reactor (1.89 cm i.d.×100 cm length) containing the same acidic mordenite zeolite (1 g) as used in the pretreatment zone. The mordenite zeolite, having a silica/alumina molar ratio of 220, is prepared as described in U.S Pat. No. 5,198,595. Benzene produced by a naphtha cracker (combination extraction unit and hydrodealkylation unit) is passed through the pretreatment zone at a rate of 100 g/h (WHSV 10 hr$^{-1}$). The temperature of the pretreatment zone is varied as described hereinbelow; pressure is maintained at 36 bar (3,600 kPa). The pretreated benzene is mixed at the inlet of the alkylation reactor with propylene. Propylene flow (WHSV) is 5.2 hr$^{-1}$; benzene/propylene molar ratio is 19.2. The alkylation feedstream comprising benzene and propylene is passed through the alkylation zone. The alkylation zone is maintained at 130° C. and 36 bar (3,600 kPa). FIG. 1 shows the effect of varying the temperature of the pretreatment zone on the yield of cumene.

It is seen in FIG. 1 that when the temperature of the pretreatment bed (guard bed) is maintained at 150° C., the alkylation catalyst maintains a steady yield of cumene. When the temperature of the pretreatment bed is lowered to 20° C. while holding the alkylation process conditions constant, the cumene yield drops significantly indicating a rapid decline in alkylation catalyst activity. When the temperature of the pretreatment bed is thereafter increased to 150° C., the yield of cumene stabilizes indicating that catalyst activity is stabilized. Note, however, that the loss in catalyst activity is irreversible. When the pretreatment bed temperature is further raised to 170° C., the deactivation rate of the alkylation catalyst is lowered even further.

Example 2

Alkylation of Benzene with Propylene to Form Cumene

The experimental setup of Example 1 is employed in the alkylation of benzene with propylene to form cumene, with the exception of the following changes. The pretreatment bed containes 20 g mordenite catalyst instead of 10 g. Benzene flow over the guard bed is 40 hr$^{-1}$. Benzene flow over the alkylation catalyst is 800 hr$^{-1}$. Propylene flow into the alkylation reactor is 12 hr$^{-1}$. Combined propylene and benzene flow through the alkylation reactor is 812 hr$^{-1}$. Benzene/propylene molar ratio is 66.7. Both the pretreatment zone and alkylation zone are started at 150° C. FIG. 2 shows the effect of varying the temperatures of the pretreatment zone and the alkylation reactor on the yield of cumene.

It is seen in FIG. 2 that when the temperature of the pretreatment bed (R1) and the alkylation reactor (R2) are maintained at 150° C., the cumene concentration in the effluent drops from 1.6 weight percent to 1.3 weight percent in about 10 hours. Thereafter, when the pretreatment bed temperature is raised to 170° C., the alkylation catalyst activity is stabilized and even increases slightly. Thereafter, when the alkylation temperature is lowered to 130° C. while maintaining the guard bed temperature at 170° C., the cumene yield drops to 0.5 percent, but the alkylation catalyst exhibits only a slow deactivation rate. When the pretreatment bed temperature is raised to 190° C., the activity of the alkylation catalyst is again stabilized. Thereafter, when the temperature of the alkylation catalyst is raised to the initial value of 150° C. and the pretreatment bed temperature is lowered to 170° C., the cumene yield increases to 1.2 weight percent and the alkylation catalyst shows little deactivation. Finally, when the temperature of the pretreatment bed is lowered to 150° C., the alkylation catalyst exhibits an increased deactivation.

The results of Examples 1 and 2 show that the temperature of the pretreatment bed plays a significant role in the deactivation rate of the alkylation catalyst. As the temperature of the pretreatment bed is raised, the deactivation rate of the alkylation catalyst decreases. Conversely, as the temperature of the pretreatment bed is lowered, the deactivation rate of the alkylation catalyst increases.

What is claimed is:

1. A process of preparing an alkylated benzene or mixture of alkylated benzenes comprising (1) contacting a benzene feedstock having a water concentration of less than 200 ppm by weight with a solid acid in a pretreatment zone at a temperature greater than 130° C. but less than 300° C. to form a pretreated benzene feedstock, and thereafter (2) contacting the pretreated benzene feedstock with (a) an alkylating agent in an alkylation zone or (b) a transalkylating agent in a transalkylation zone, the contacting occurring in the presence of an alkylation/transalkylation catalyst selected from the group consisting of acidic mordenite, acidic beta zeolite, acidic Y zeolite, acidic omega zeolite, acidic L zeolite, and crystalline magnesium silicates, under liquid phase reaction conditions sufficient to produce the alkylated benzene or mixture of alkylated benzenes.

2. The process of claim 1 wherein the benzene feedstock is unsubstituted benzene.

3. The process of claim 1 wherein the benzene feedstock is a substituted benzene containing at least one substituent selected from the group consisting of alkyl and hydroxyl moieties.

4. The process of claim 1 wherein the solid acid is selected from the group consisting of acidic aluminas, silicas, silica-aluminas, clays, zeolites, and mesoporous aluminosilicates.

5. The process of claim 1, wherein the solid acid is an aluminosilicate selected from the group consisting of ZSM-5, ZSM-11, ZSM-35, clinoptilolite, ferrierite, stilbite, EU-1, NU-87, mordenite, omega, beta, faujasites, gmelinite, ZSM-12, cancrinite, L, MCM-22, MCM-41, MCM-49, MCM-56, and MCM-58.

6. The process of claim 5 wherein the silica/alumina molar ratio of the aluminosilicate ranges from about 5 to about 10,000.

7. The process of claim 1 wherein the contacting is conducted at a temperature in the pretreatment bed of greater than about 150° C. and less than about 250° C., a pressure ranging from about 1 bar to about 45 bar, and a space velocity of the benzene feedstock ranging from about 0.1 hr$^{-1}$ to about 1000 hr$^{-1}$.

8. The process of claim 1 wherein a wet benzene feedstock is passed over a drying agent so as to reduce the water concentration to less than 200 ppm by weight, prior to pretreatment of the benzene feedstock over the solid acid.

9. The process of claim 8 wherein the drying agent is selected from the group consisting of silicas, aluminas, silica-aluminas, and zeolites.

10. The process of claim 9 wherein the temperature of the drying agent ranges from about 10° C. to about 90° C.

11. The process of claim 1 wherein a wet benzene feedstock is dried by purging with an inert gas zone, so as to reduce the water concentration to less than 200 ppm by weight, prior to entry of the benzene feedstock into the pretreatment zone.

12. The process of claim 1 wherein a wet benzene feedstock is dried by azeotropic distillation, so as to reduce the water concentration to less than 200 ppm by weight, prior to pretreatment of the benzene feedstock.

13. The process of claim 1 wherein the alkylating agent or transalkylating agent is purged with an inert gas prior to entry into the alkylation or transalkylation zone.

14. The process of claim 1 wherein the alkylating agent is an olefin having from two to about twelve carbon atoms.

15. The process of claim 14 wherein the alkylating agent is ethylene or propylene.

16. The process of claim 1 wherein the transalkylating agent is a polyalkylated benzene.

17. The process of claim 16 wherein the transalkylating agent is polyethylbenzene or poly(isopropyl)benzene.

18. The process of claim 1 wherein the alkylation/transalkylation catalyst is mordenite, beta, Y, or a porous crystalline magnesium silicate.

19. The process of claim 1 wherein the alkylation/transalkylation catalyst is an acidic mordenite having a silica/alumina molar ratio of at least 30/1 and a Symmetry Index, as determined by X-ray diffraction, of at least about 1.0 and wherein the acid mordenite is prepared by a method comprising (1) calcining in air or heating in an inert atmosphere an acid mordenite having a silica/alumina molar ratio less than 30/1 and a Symmetry Index in the range from 0.5 to about 1.3, and thereafter (2) treating the calcined or heated mordenite with a strong acid under reaction conditions sufficient to increase the silica/alumina molar ratio to at least 30/1 and (3) repeating the steps of (1) calcining or heating and (2) strong acid treating at least once to remove additional alumina.

20. The process of claim 1 wherein the contacting is conducted at an alkylation temperature ranging from about 100° C. to about 300° C. and a pressure ranging from about 10 bar to about 200 bar.

21. The process of claim 1 wherein the contacting is conducted at a transalkylation temperature ranging from about 140° C. to about 300° C. and a pressure ranging from about 10 bar to about 200 bar.

22. A process of preparing ethylbenzene or cumene comprising (1) drying a wet benzene feedstock under conditions such that water in the feedstock is reduced to a concentration of less than 200 ppm by weight, the drying being effected by:

(a) contacting the wet benzene feedstock with a drying agent, or (b) purging the wet benzene feedstock with an inert gas, or (c) subjecting the wet benzene feedstock to azeotropic distillation; and then (2) contacting the dried benzene with a zeolite or a mesoporous aluminosilicate in a pretreatment zone at a temperature greater than 130° C. but less than 300° C. to form a pretreated benzene, and thereafter (3) contacting the pretreated benzene with ethylene or propylene in an alkylation zone, the contacting occurring in the presence of an alkylation catalyst selected from the group consisting of acidic mordenite, acidic beta zeolite, acidic Y zeolite, acidic omega zeolite, acidic L zeolite, and porous crystalline magnesium silicates, the contacting being conducted under liquid phase conditions at a temperature ranging from about 100° C. to about 300° C. and a pressure ranging from about 10 bar to about 200 bar so as to produce ethylbenzene or cumene.

23. A process of increasing the lifetime of an alkylation/transalkylation catalyst employed in the alkylation of a benzene feedstock with an alkylating agent, or employed in the transalkylation of a benzene feedstock with a polyalkylated benzene, the process comprising contacting a benzene feedstock having a water concentration of less than 200 ppm by weight with a solid acid selected from the group consisting of acidic aluminas, silicas, silica-aluminas, clays, zeolites and mesoporous aluminosilicates at a temperature greater than 130° C. but less than 300° C. prior to the benzene feedstock participating in liquid phase alkylation or transalkylation using an alkylation/transalkylation catalyst selected from the group consisting of acidic mordenite, acidic beta zeolite, acidic Y zeolite, acidic omega zeolite, acidic L zeolite, and crystalline magnesium silicates.

* * * * *